United States Patent
Han et al.

(10) Patent No.: US 10,446,274 B2
(45) Date of Patent: Oct. 15, 2019

(54) OPEN HEALTHCARE APPARATUS AND METHOD

(71) Applicant: ELECTRONICS AND TELECOMMUNICATIONS RESEARCH INSTITUTE, Daejeon (KR)

(72) Inventors: Young-Woong Han, Daejeon (KR); Young-Won Kim, Daejeon (KR); Myung-Eun Lim, Daejeon (KR); Ho-Youl Jung, Daejeon (KR); Jae-Hun Choi, Daejeon (KR); Dae-Hee Kim, Daejeon (KR); Min-Ho Kim, Daejeon (KR); Seung-Hwan Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 450 days.

(21) Appl. No.: 14/949,656

(22) Filed: Nov. 23, 2015

(65) Prior Publication Data
US 2016/0147975 A1    May 26, 2016

(30) Foreign Application Priority Data

Nov. 25, 2014 (KR) .................. 10-2014-0165381
Feb. 26, 2015 (KR) .................. 10-2015-0027332
Jul. 21, 2015 (KR) .................. 10-2015-0103248

(51) Int. Cl.
G06F 19/00 (2018.01)
G16H 50/70 (2018.01)

(52) U.S. Cl.
CPC .................. *G16H 50/70* (2018.01)

(58) Field of Classification Search
CPC ..... H04L 67/2823; G06F 19/32; G06F 19/00; G06F 19/321; G06F 19/328;
(Continued)

(56) References Cited

U.S. PATENT DOCUMENTS

2011/0106564 A1* 5/2011 Hachmeister .......... G06Q 10/00
                                                          705/3
2014/0195268 A1    7/2014 Lim et al.
(Continued)

FOREIGN PATENT DOCUMENTS

KR    10-2006-0037528 A    5/2006
KR    1020090046290 A      5/2009
(Continued)

OTHER PUBLICATIONS

Hyuncheol Yang et al., "Manual for utilizing Big Data Technology and procedures for each phase of utilization of Big Data", May 20, 2014, Ministry of Science, ICT and Future Planning, Korea.
(Continued)

*Primary Examiner* — Maroun P Kanaan

(57) ABSTRACT

Disclosed herein is an open healthcare apparatus and method in which a user personally performs integrated management of health records including data concerning western medicine, oriental medicine, life logs, etc. health-related big data is built by receiving health information, from which personal information is deleted, under the agreement of the user, and customized health service is provided by various service providers based on the health-related big data. The disclosed apparatus includes a personal cloud repository for storing personal health data, a health-related big data repository for storing public and personal health data on a health case basis, a healthcare platform for storing and analyzing personal health data and for relaying and managing a customized service, and an analysis platform for analyzing user's health based on the information of the health-related
(Continued)

big data repository and for providing customized service depending on the analysis result.

11 Claims, 12 Drawing Sheets

(58) Field of Classification Search
CPC ............. G06F 19/3418; G06F 21/6218; G06F 21/6245; G06F 21/64; G06F 21/31; G06Q 50/24; G16H 10/60; G16H 10/65; G16H 50/70; G16H 40/20
See application file for complete search history.

(56) References Cited

U.S. PATENT DOCUMENTS

| | | | |
|---|---|---|---|
| 2014/0244278 A1 | | 8/2014 | Park et al. |
| 2015/0213225 A1* | | 7/2015 | Amarasingham ... G06F 19/3431 705/2 |

FOREIGN PATENT DOCUMENTS

| | | |
|---|---|---|
| KR | 10-2009-0101561 A | 9/2009 |
| KR | 10-2012-0010747 A | 2/2012 |
| KR | 10-2013-0001500 A | 1/2013 |
| KR | 10-2013-0029576 A | 3/2013 |

OTHER PUBLICATIONS

Taemin Song et al., "2013 Development and Operation of Gateway system for Internet Health Information", National Digital Science Library, Dec. 31, 2013, Korea Institute for Health and Affairs.

\* cited by examiner

OPEN HEALTHCARE APPARATUS AND METHOD

CROSS REFERENCE TO RELATED APPLICATIONS

This application claims the benefit of Korean Patent Application No. 10-2014-0165381, filed Nov. 25, 2014, No. 10-2015-0027332, filed Feb. 26, 2015, and No. 10-2015-0103248, filed Jul. 21, 2015, which are hereby incorporated by reference in their entirety into this application.

BACKGROUND OF THE INVENTION

1. Technical Field

The present invention generally relates to an open healthcare apparatus and method. More particularly, the present invention relates to an open healthcare apparatus and method that may provide a customized health service based on health cases and health information managed by individuals.

2. Description of the Related Art

The conventional arts concerning personal health record management involve a process of accessing the server of a single specific medical institution, receiving personal health records after user authentication, and storing the records in a personal terminal device.

Accordingly, the conventional arts have a system in which the main agent of healthcare is the specific medical institution that provides the health records, rather than the individual.

Also, referring to Korean Patent Application Publication No. 2013-0001500, titled "System and method for managing personal health record", and Korean Patent Application Publication No. 2013-0029576, titled "Method for serving health-related information and POI information based on cloud and system therefor", personal health records focus on the management of Electronic Medical Records (EMR), which pertain to western medicine.

In order to enable individuals having personal health records to actively manage their health records, the individuals should be able to acquire their EMR from various clinics that have provided medical healthcares to the individuals. Also, a method for performing integrated management of the personal health records acquired from oriental medical institutions and life log servers and devices is required. However, currently, there is a lack of technology for integrated management of personal health records, and there has not been defined a health record format for integrated management capable of accommodating various forms of personal health records, including data concerning western and oriental medicine, life logs, and the like.

Also, a technique for effectively storing and managing collected personal health records is absent. Korean Patent Application Publication No. 2013-0001500 discloses a method for storing personal health records transmitted from medical institutions in a portable terminal, but has a limitation in its inability to store large amounts of time-series health records.

Meanwhile, existing healthcare services individually provide services in different forms. Because a healthcare service is a data-based information service and the quantity and quality of data are very important for providing reliable information, the existing services are limited in that they have different forms.

For successful healthcare service, what is required is an open healthcare platform based on which users may use various services by providing their health records and service providers may provide reliable and various services based on big data pertaining to users' health.

SUMMARY OF THE INVENTION

Accordingly, the present invention has been made keeping in mind the above problems occurring in the conventional art, and an object of the present invention is to provide an open healthcare apparatus and method based on which individuals may perform integrated management of their health records, including data about western and oriental medicine and life logs, health-related big data are accumulated by receiving health information from which personal information has been deleted, and various service providers may provide customized health services based on the health-related big data.

In order to accomplish the above object, an open healthcare apparatus according to an aspect of the present invention includes a healthcare platform for providing an Open API enabling provision of a customized service, the healthcare platform including a personal health data processing unit for receiving personal health data from at least one health record provider to be stored in a personal cloud repository and a public health data processing unit for receiving public health data from a public health data server to be stored in a health-related big data repository on a health case basis.

Also, the open healthcare apparatus includes an analysis platform comprising a health data analysis unit for analyzing personal health data of a user based on information of the health-related big data repository and a health analysis result provision unit for providing a health data analysis result of the health data analysis unit to the healthcare platform to provide the user with a customized service.

The personal health data processing unit converts the personal health data, provided from a personal health data server, into a format of a health record by performing communication, authentication, and data transmission with the health record provider through the healthcare platform.

Also, the public health data processing unit receives the public health data from the public health data server, and the received public health data is converted into a format of a health record through the public health data processing unit and stored in the health-related big data repository.

The format of the health record is an XML format.

The health-related big data repository stores health data provided by the personal cloud repository under agreement of the user, the public health data provided by the public health data server, or a combination thereof.

The health data analysis unit is configured to: retrieve a case similar to health data of the user by mining the information of the health-related big data repository; predict future health of the corresponding user based on the retrieved similar case; and propose a guideline for improving health.

The health record provider includes a server of at least one western medicine hospital, a server of at least one oriental medicine hospital, a life log server, or a combination thereof.

An open healthcare method performed by an open healthcare apparatus according to an embodiment of the present invention includes: receiving personal health data from at least one health record provider, storing the personal health data in a personal cloud repository, and performing integrated management on the personal health data; analyzing personal health data using health-related big data that includes public health data and the personal health data in the personal cloud repository; and providing a customized health service based on the analyzed personal health data.

Performing integrated management comprises converting the personal health data, provided from the health record provider, into a format of a health record by performing communication, authentication, and data transmission with a personal health data server through a healthcare platform.

The open healthcare method further include receiving the public health data from a public health data server, wherein the received public health data is converted into a format of a health record by a public health data processing unit and is stored in a health-related big data repository.

Performing integrated management is configured to store the received personal health data in the personal cloud repository by transmitting the data to the personal cloud repository through health data relay by a healthcare platform rather than storing the data in a portable terminal of a user.

The health-related big data is health data, provided by the personal cloud repository under agreement of a user, the public health data, provided by a public health data server, or a combination thereof.

Providing the customized health service comprises retrieving a case similar to health data of a corresponding user by performing data mining on the health-related big data; and predicting future health of the corresponding user based on the retrieved similar case, and proposing a guideline for improving health.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
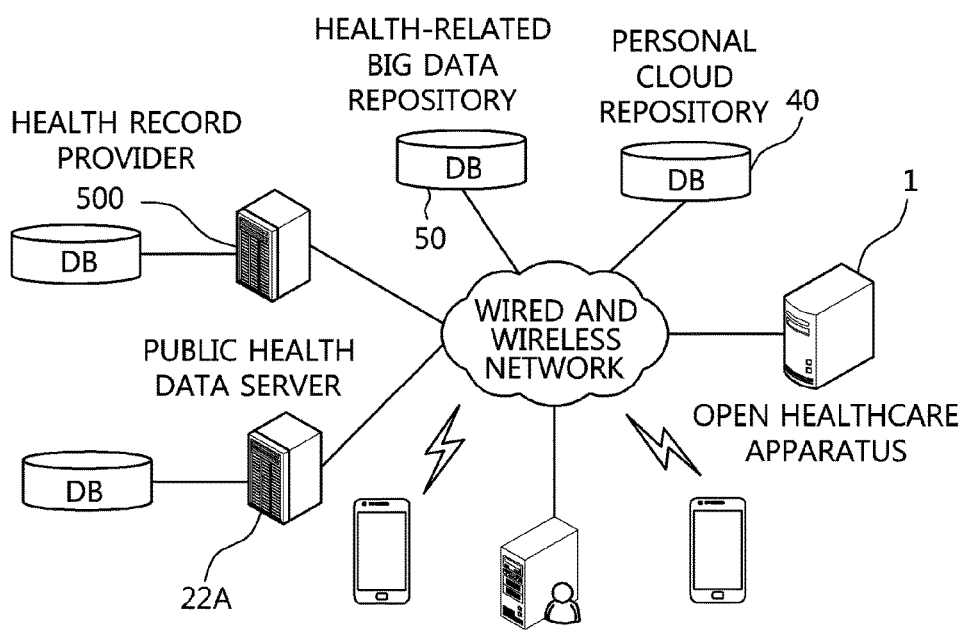
FIG. 1 is a block diagram illustrating the configuration for providing the service of an open healthcare apparatus according to an embodiment of the present invention.

The present invention may be variously changed, and may have various embodiments, and specific embodiments will be described in detail below with reference to the attached drawings.

However, it should be understood that those embodiments are not intended to limit the present invention to specific disclosure forms and they include all changes, equivalents or modifications included in the spirit and scope of the present invention.

The terms used in the present specification are merely used to describe specific embodiments and are not intended to limit the present invention. A singular expression includes a plural expression unless a description to the contrary is specifically pointed out in context. In the present specification, it should be understood that terms such as "include" or "have" are merely intended to indicate that features, numbers, steps, operations, components, parts, or combinations thereof are present, and are not intended to exclude the possibility that one or more other features, numbers, steps, operations, components, parts, or combinations thereof may be present or added.

Unless differently defined, all terms used here including technical or scientific terms have the same meanings as the terms generally understood by those skilled in the art to which the present invention pertains. The terms identical to those defined in generally used dictionaries should be interpreted as having meanings identical to contextual meanings of the related art, and are not interpreted as having ideal or excessively formal meanings unless they are definitely defined in the present specification.

Embodiments of the present invention will be described in detail with reference to the accompanying drawings. In the following description of the present invention, the same reference numerals are used to designate the same or similar elements throughout the drawings, and repeated descriptions of the same components will be omitted.

In the conventional art, information about personal health records has been stored and managed in databases privately owned by various health service institutes (for example, hospitals, oriental medical clinics, fitness centers, personal healthcare apparatuses, and the like). This means that the information about personal health records is scattered around various service institutes, whereby the integrated management thereof is difficult. Also, it is difficult for users to be provided with services from the different institutes due to the lack of interoperability, which is attributable to the different data formats used by the respective service institutes.

Furthermore, because institutes providing health services construct and manage different application platforms for providing their own services, users must use the different platforms, managed by each of the health service providing institutes, and different apps, provided by the platforms, in order to use various health services.

Therefore, required is an integrated platform in which information about personal health records is converted into a consistent format that may be accommodated by all the service institutes, the information about personal health records is integrated and managed by individuals rather than respective institutes, and various customized health services can be provided based on the information about personal health records.

In order to solve the above problems, the present invention intends to propose an open healthcare apparatus and method using a healthcare platform.

Hereinafter, an open healthcare apparatus according to an embodiment of the present invention is described.

FIG. 1 is a block diagram illustrating the configuration for providing a service of an open healthcare apparatus according to an embodiment of the present invention.

An open healthcare apparatus 1 according to an embodiment of the present invention collects personal health data and public health data by connecting to at least one health record provider 500 and a public health data server 22A through wired and wireless networks, supported by an app installed in a user terminal, converts the collected data into a format convenient for use, stores the converted data in a personal cloud repository 40 and a health-related big data repository 50, and provides customized health service to the corresponding user in response to requests from the user terminal.

The health record provider 500 may have its own database or manage a database in the cloud, and the public health data server 22A may manage data in the same manner as the health record provider 500.

Also, the health record provider 500 indicates a personal health service institute (for example, a hospital, an oriental medicine clinic, a fitness center, etc.) that stores and manages information about personal health records that are written when a user is normally provided with personal health service.

Also, the user may be provided with service by accessing the open healthcare apparatus 1 using a wired or wireless terminal via wired and wireless networks, or may be provided with an open healthcare service by personally downloading and executing the management app 30 of the open healthcare apparatus 1 according to the present invention.

Figure 2:
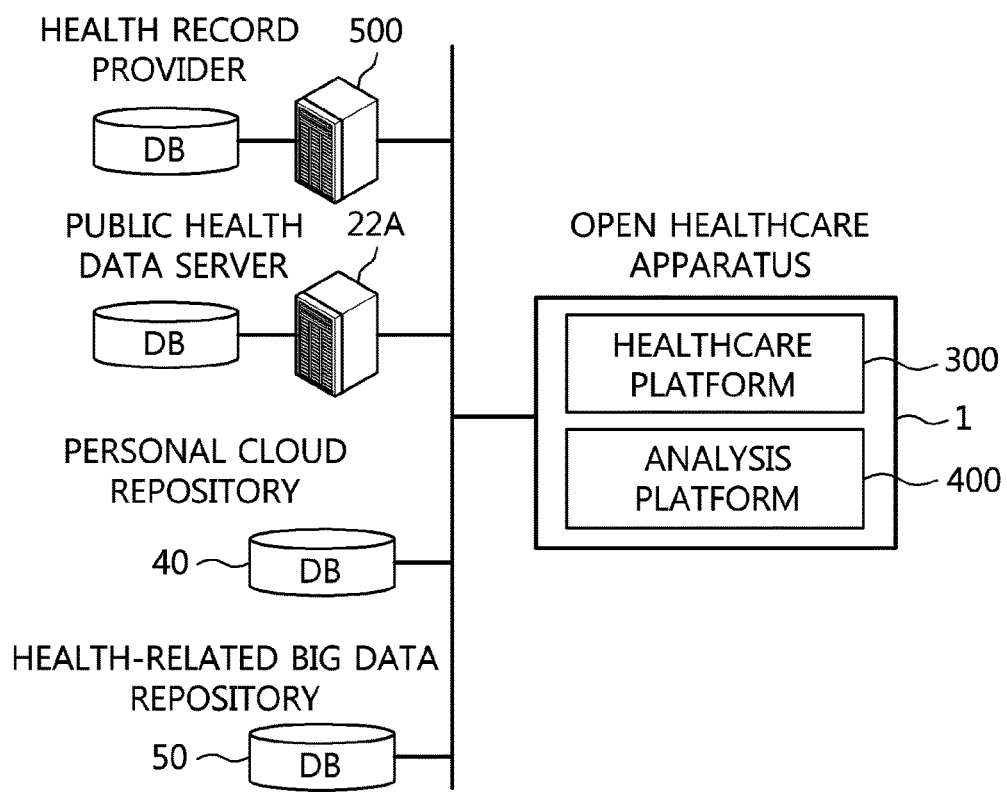
FIG. 2 is a block diagram of the internal configuration of an open healthcare apparatus according to an embodiment of the present invention.
Figure 3:
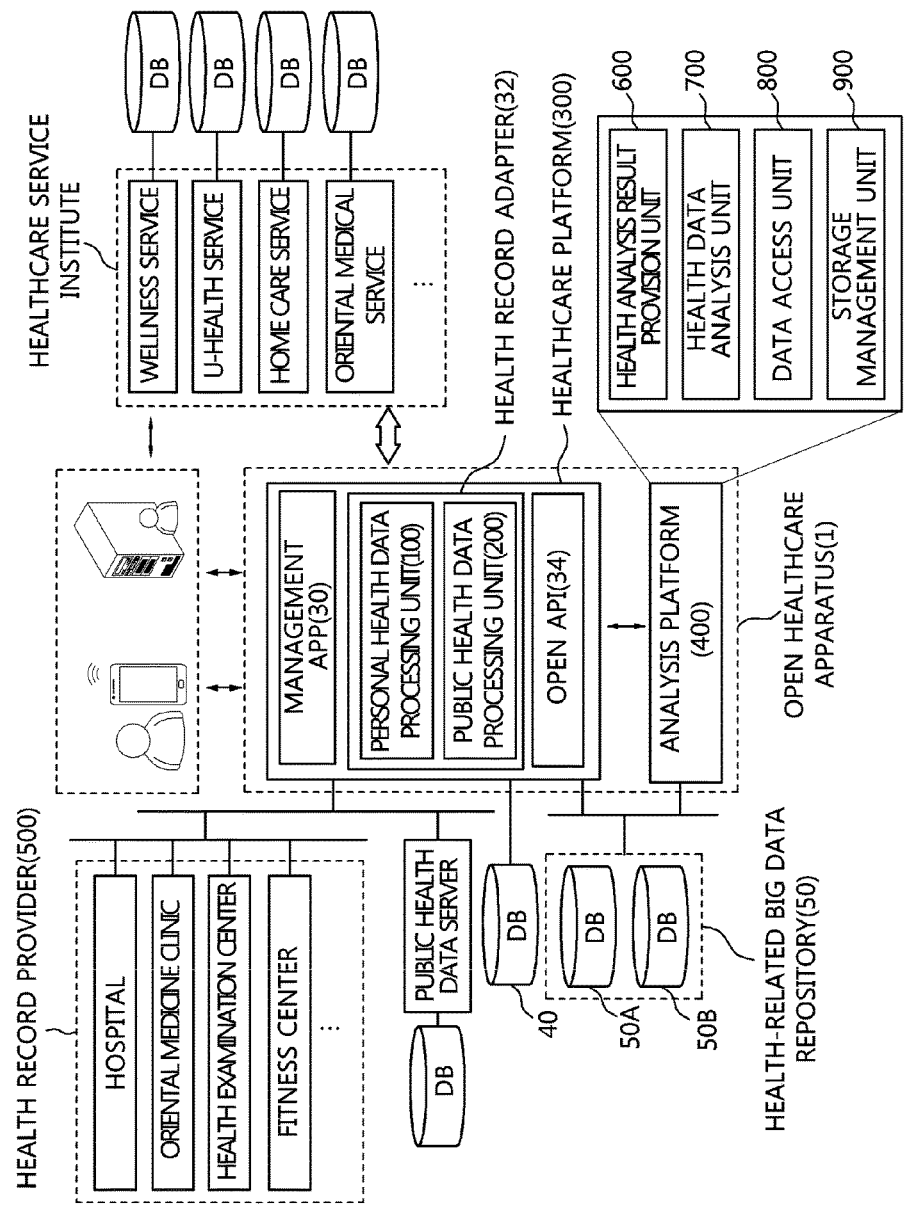
FIG. 3 is a block diagram of the healthcare platform and analysis platform of a healthcare apparatus according to an embodiment of the present invention.

FIG. 2 is a block diagram of the internal configuration of an open healthcare apparatus according to an embodiment of the present invention, and FIG. 3 is a block diagram of the healthcare platform and analysis platform of a healthcare apparatus according to an embodiment of the present invention.

As illustrated in FIG. 2, an open healthcare apparatus 1 according to an embodiment of the present invention includes a healthcare platform 300 and an analysis platform 400. As illustrated in FIG. 3, the healthcare platform 300 provides an Open API 34 for interconnecting the health record provider 500, user terminals, healthcare service institutes, and the like, and provides a health record adapter 32 for relaying data transmitted during the process for performing the above function.

Also, the healthcare platform 300 includes a personal health data processing unit 100, a public health data processing unit 200, the Open API 34, and a management app 30.

Also, the personal health data processing unit 100 may receive data such as personal Electronic Medical Records (EMRs) about western and oriental medicine, life logs, and the like, from the at least one health record provider 500.

That is, the personal health data processing unit 100 receives personal health data from the health record provider 500, which manages personal health data, for example, servers of one or more western medical hospitals, servers of one or more oriental medicine hospitals (including oriental medicine clinics), life log servers (or devices), etc. In the conventional art, the server of a specific medical institute is accessed, the user is authenticated, and personal EMR data are transferred to a terminal device of the user or delivered to another medical institute. However, the present invention may simply interconnect with various medical institutes and retrieve personal health records from multiple hospitals, oriental medicine clinics, and life log servers, through an interface unified based on the healthcare platform 300, thus enabling integrated management.

For the integrated management of various forms of health records, the present invention converts data about western medicine and oriental medicine and life log data into health records in an XML format. To this end, the healthcare platform 300 may interconnect with various health record providers 500.

As an example of the health record provider 500, FIG. 3 illustrates only a hospital, an oriental medicine clinic, a health examination center, and a fitness center, but there may be other health record providers. Also, each health record provider 500 is connected to a network, and the personal health data processing unit 100 receives personal health data from the health record provider.

The personal health data processing unit 100 serves to convert personal health data by interconnecting with multiple health record providers 500. Through the personal health data processing unit 100, the health record provider 500 performs communication with the healthcare platform 300, authentication, and data transmission. In order to analyze data collected from the health record provider 500, the personal health data processing unit 100 transmits the collected personal health record data to the analysis platform 400, receives the personal health record data (that is, health data) analyzed by the analysis platform, and converts the received data into an XML format to be provided to the user.

Also, the public data processing unit 200 receives public health data from the public health data server 22A. Although FIG. 2 illustrates only one public health data server 22A, a plurality of public health data servers 22A may be connected to a network, and the public health data processing unit 200 may receive public health data from them.

In Korea, the public health data processing unit 200 may receive a large amount of health data from public health data servers 22A of the National Health Insurance Corporation, the Health Insurance Review and Assessment Service, and the like. Also, the public health data processing unit 200 may convert the health data (that is, health records) provided by the public health data server 22A into a predetermined XML format. Also, the public health data of the public health data processing unit 200 is stored in the health-related big data repository 50.

The healthcare platform 300 serves to store personal health data, open the health data managed by users, analyze the personal health data, and relay and manage customized services.

When a user joining the healthcare platform 300 executes a command for importing a personal health record in the portable terminal of the user, the healthcare platform 300 may retrieve the personal health record by communicating with a health record provider 500 selected by the user. In this case, the retrieved health record is not stored in the portable terminal but is transmitted to the personal cloud repository 40 to be stored by the personal health data processing unit 100 through the health data relay function of the healthcare platform 300.

The healthcare platform 300 includes the Open API 34 for performing the health data relay function. The health data relay function includes task processing, data relay, authentication, and the like, between the personal health data processing unit 100, the personal cloud repository 40, a health analysis result provision unit 600, and a health data analysis unit 700. Also, the Open API provides an environment in which a customized service using personal health records and health-related big data is provided thanks to the participation of various health service providers.

As described above, users retrieve their personal health records from the health record provider 500 and perform integrated management of the records in the personal cloud repository 40 by themselves, and the data is provided under the agreement of the users. Therefore, the process for providing various customized health services based on health-related big data is performed and managed in the healthcare platform 300.

The personal cloud repository 40 stores personal health data. Namely, the personal health data retrieved from the health record provider 500 is stored in the personal cloud repository 40 rather than the portable terminal Because the personal cloud repository 40 may store a large amount of data, be stable, and guarantee security by allowing access through user authentication, it is suitable for storing and managing health examination data, clinical image data, life logs, and the like.

Under the agreement of a user, the health-related big data repository 50 may store health data in which personally identifying information is deleted or substituted. Also, the health-related big data repository 50 stores not only the personal health data but also public health data. Data stored in the health-related big data repository 50 is a large amount of time-series health records, and may be stored on a health case basis. That is, the data in the health-related big data repository 50 may be referred to as big data.

The health-related big data repository 50 is used by the analysis platform 400.

Also, the health-related big data repository 50 may separately store data provided by individuals and data provided by public institutes in order to facilitate the retrieval of health data used for analysis, performed by the analysis platform 400.

In other words, the health data may be stored separately in a personal health record big data repository 50A for storing health data, in which personally identifying information is deleted or substituted, under the agreement of the user, and also in a baseline public clinic big data repository 50B for storing public health data provided by public institutes.

The analysis platform 400 may retrieve similar health cases and provide information for predicting health by analyzing personal health data based on the health data in the health-related big data repository 50. Namely, through mining of the health-related big data, the analysis platform 400 may perform an analysis process such as retrieving similar cases, predicting health, and providing guidelines for improving health.

Based on these analysis results, the analysis platform 400 may provide various customized health services. Also, the analysis platform 400 may provide a healthcare service in the form of an independent app by interworking with the healthcare platform 300.

Because it is very important to build and analyze a large amount of time-series health data in order to provide a reliable customized health service, the present invention constructs the health-related big data repository 50 using both the personal and public health cases, and manages it by continuously updating data.

Meanwhile, an open healthcare method according to an embodiment of the present invention includes a step in which a user retrieves his or her health records from the health record provider 500 and performs integrated management of the health records in the personal cloud repository 40 and a step in which various customized health services are provided based on personal and public health-related big data.

Hereinafter, an open healthcare method according to an embodiment of the present invention is described with reference to FIG. 3.

As illustrated in FIG. 3, the healthcare platform 300 provides the Open API 34 for interconnecting the health record provider 500, user terminals, health management service institutes, and the like, and provides the health record adapter 32, which functions as a framework for relaying data transmitted during the process for performing the above function.

Also, the health record adapter 32 may be configured to include a personal health data processing unit 100 for storing personal health data, provided by at least one health record provider 500, in the personal cloud repository 40 and for providing users with the result of analysis of the personal health data, and a public health data processing unit 200, for receiving public health data from a plurality of public health data servers and storing them in the health-related big data repository.

Also, the user terminal requests personal health data of a user from at least one health record provider 500, selected by the user, by interworking with the personal health data processing unit 100 of the healthcare platform 300, and stores the data in the personal cloud repository 40 after user authentication through the personal health data processing unit 100. Meanwhile, the personal cloud repository 40 enables the user to personally store and manage the personal health records, and may be a storage device having high security and stability by allowing access through user authentication.

Also, the health record adapter 32 converts information about personal health records, which is distributed and managed by different service institutes, into a health record having a consistent format that may be accommodated by all the institutes, and stores it in the personal cloud repository 40.

Also, the health record has a data format that enables all the institutes to manage and use the data without data conversion, and may represent health records of various fields, for example, medical care, oriental medicine, life logs, and the like.

Also, the health record is personal health data received from each health record provider 500. For example, if the health record provider 500 is a hospital, an oriental medicine clinic, or a fitness center, the health record may be the EMR of the hospital, the record related to oriental medicine, or fitness data including personal biometric data, respectively. Additionally, personal life log data, data about the condition of a person having a chronic disease, and the like may be provided by various service institutes.

Also, the identical data format may be an XML format, which is extended based on ASTM CCR, which is an international standard, or may be a data standard defined by another method. The present invention does not limit the method for defining the identical data format that enables all the institutes to accommodate the personal health record, and hereinafter, the personal health data is referred to as a health record in which data is converted into the identical data format.

Also, the health record provider 500 may include a hospital, a health examination center, an oriental medicine clinic, a fitness center, and the like, and may convert the personal health data requested by the user into the health record to be provided. Also, the personal health data may be converted into the health record by the health record provider 500 or the health record adapter 32, provided by the healthcare platform 300, and stored in the personal cloud repository 40.

Also, because the health record may be personally managed by a user, when requesting a healthcare service from a healthcare service institute, the user may voluntarily provide his or her health records to the healthcare service institute. Also, the provided health records may be used as personal health record big data in order to provide various customized healthcare services based on the personal health record.

Also, as described above, the healthcare platform 300 interconnects the health record provider 500, user terminals, health management service institutes, and the like, to implement various functions such as importing health records, retrieving health records, and providing a customized healthcare service based on the personal health records, and relays data, transmitted during the process of performing the above functions.

Also, the healthcare platform 300 may provide the management app 30 to the user terminal, and the management app 30 may support functions such as retrieving personal health data from the health record provider 500, retrieving personal health records from the personal cloud repository 40, and the like. Meanwhile, the management app 30 is provided by the healthcare platform 300, and a service app for providing the service of a healthcare service institute may perform the same process as the management app 30. Also, the healthcare service institute may provide the service app to provide the service thereof, and the user may install the app in the user terminal by personally accessing the server of the healthcare service institute or through an app store provided by the healthcare platform 300.

Also, through interworking with the analysis platform 400, the healthcare platform 300 receives analytical data customized to a user, which is analyzed by the analysis platform 400, and provides the data to the user terminal.

Also, the analysis platform 400 includes a health data analysis unit 700 for analyzing personal health data based on data stored in the personal health record big data repository and baseline public clinic big data repository and a health analysis result provision unit 600 for providing the result of the health data analysis, performed by the health data analysis unit, to the healthcare platform 300.

Also, the health data analysis unit 700 serves to analyze personal health records enabling the healthcare services provided by various healthcare service institutes. Also, the health data analysis unit 700 retrieves information about changes in the user's health based on the data stored in the health-related big data repository 50, and generates information predicting the future health of the user. The generated information provides the healthcare service institutes with important analytical functions required for the development of a health planning service such as lifestyle planning for improving health.

Also, the analysis platform 400 may further include a storage management unit 900 for converting a personal health record, in which personal information is deleted or substituted, into a common data format that may be accommodated by all the institutes in order to store the personal user records in the personal health record big data repository 50A, and a data access unit 800, for using the data stored in the health big data repository to predict changes in the future health of a user based on the health records of the user.

Meanwhile, the personal health record big data repository 50A is a device for accumulating and storing the health records in the personal cloud repository 40 under the agreement of each user, and the baseline public clinic big data repository 50B is a device for storing data provided by the National Health Insurance Corporation, the Health Insurance Review and Assessment Service, and the like, in Korea. Here, the data stored in the baseline public clinic big data repository 50B are health records generated for a large group of people, and the repository is a device for storing cohort sample data.

Also, the personal health record big data repository 50A and the baseline public clinic big data repository 50B may be provided to the analysis platform 400 to make it possible to predict changes in the future health of a user using the personal health data of the user.

Also, as described above, the personal health record big data repository 50A and the baseline public clinic big data repository 50B may be stored in a single health-related big data repository 50, and may be provided by the healthcare platform 300, or may be constructed on a network like the personal cloud repository 40.

The present invention intends to propose an open healthcare apparatus and method for providing various customized healthcare services based on personal health records by enabling individuals to perform integrated management of their health records using the above-mentioned healthcare platform 300 and by opening the health records managed by the individuals.

Figure 4:
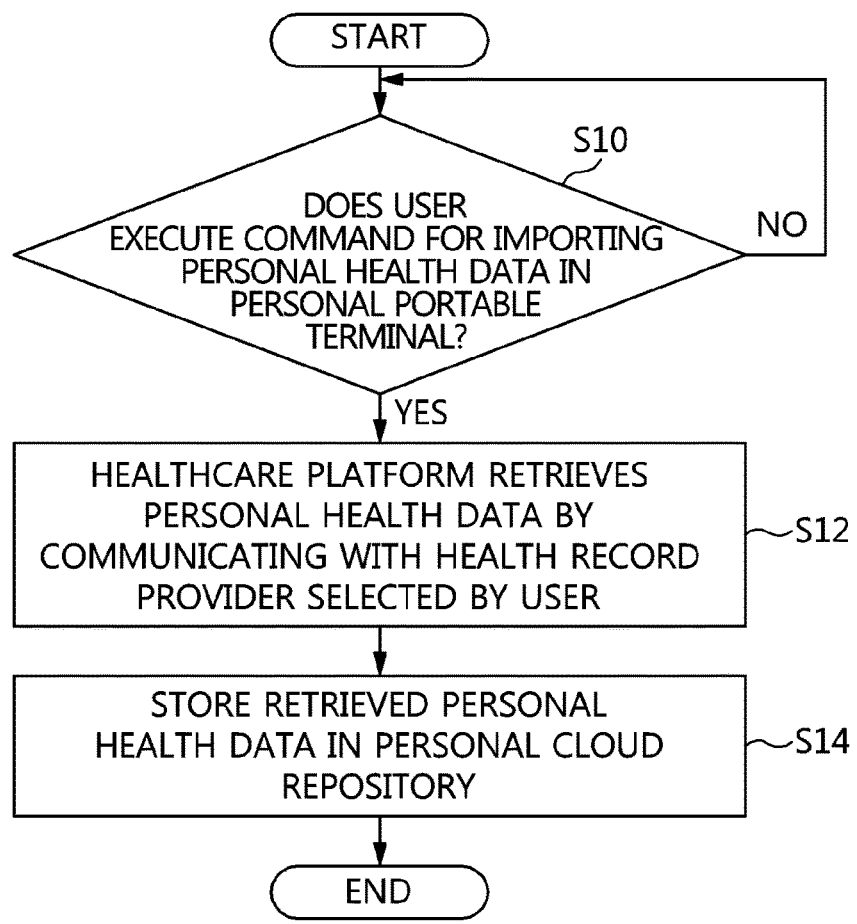
FIG. 4 is a flowchart illustrating a health data management process managed by individuals, in an open healthcare method according to an embodiment of the present invention.

First, a health data management process managed by individuals in an open healthcare method according to an embodiment of the present invention is described with reference to FIG. 4.

The personal health data processing unit 100 receives personal health data from health record providers 500, including multiple hospitals, oriental medicine clinics, life log devices and servers, etc.

The personal health data processing unit 100 converts the received data about western medicine, oriental medicine, and life logs into an XML format, and stores the data in the personal cloud repository 40 through the healthcare platform 300.

Specifically, when a user joining the healthcare platform 300 executes a command for importing personal health records in a personal portable terminal ("Yes" at step S10), the healthcare platform 300 communicates with the health record provider 500 and retrieves the personal health records of the corresponding user (that is, health records related to western medicine, oriental medicine, and life logs) at step S12.

Then, the open healthcare platform 300 does not store the retrieved health records in the portable terminal of the corresponding user, but transmits them to the personal cloud repository 40 to be stored through the health data relay function of the healthcare platform 300 at step S14.

Accordingly, individuals may perform integrated management of their health records concerning western medicine, oriental medicine, and life logs.

Figure 5:
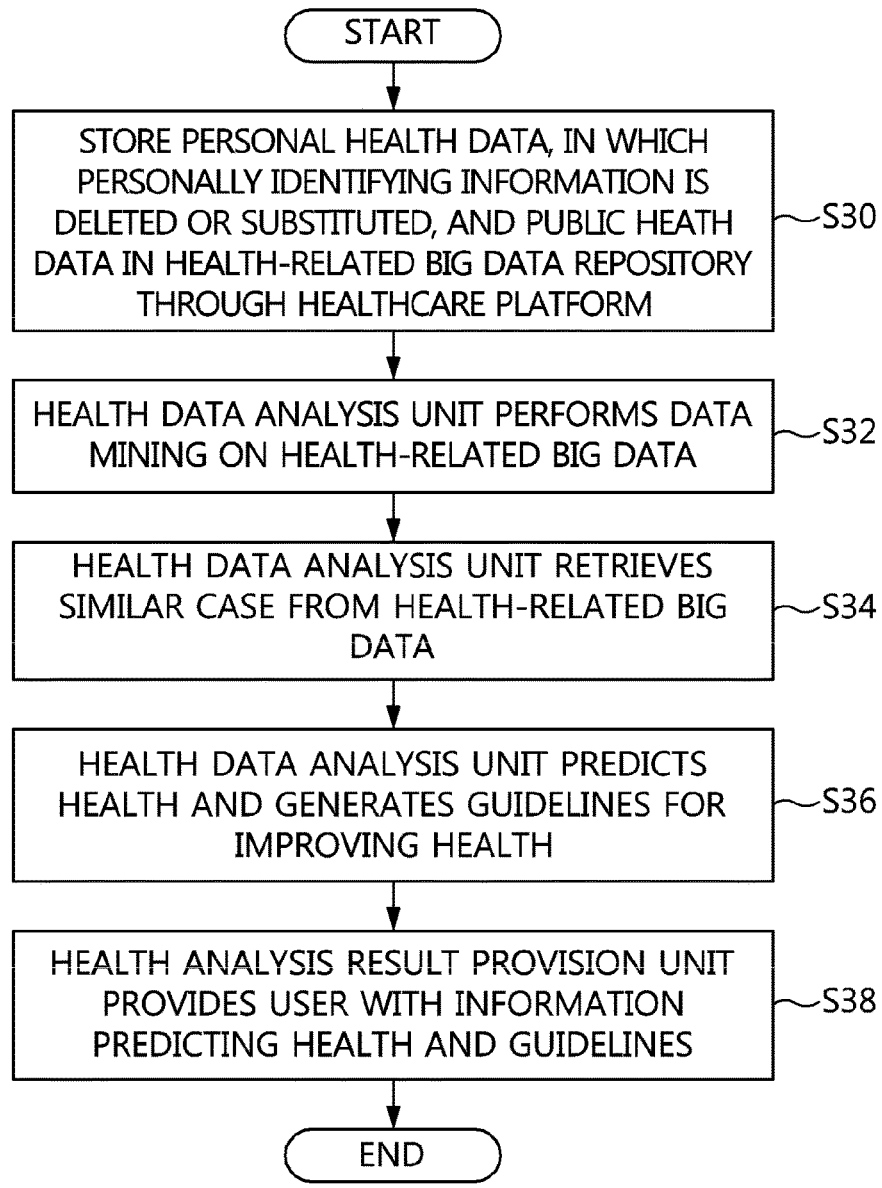
FIG. 5 is a flowchart illustrating a process for providing customized health service based on health cases in an open healthcare method according to an embodiment of the present invention.

Hereinafter, a process for providing a customized health service based on health cases in an open healthcare method according to an embodiment of the present invention is described with reference to FIG. 5.

According to the present invention, when a user agrees to make his or her health records available, various customized healthcare services may be provided.

First, under the agreement of the user, health records, in which personally identifying information is deleted or substituted, are stored in the health-related big data repository 50. Here, the health-related big data repository 50 stores not only personal health data but also public health data at step S30.

In order to provide a customized health service based on health cases to the user who joined the healthcare platform 300, the health data analysis unit 700 of the analysis platform 400, which is connected to the healthcare platform 300, performs data mining on the health-related big data of the health-related big data repository 50 at step S32.

Then, the health data analysis unit 700 retrieves cases similar to the health records of the corresponding user at step S34.

Then, the health data analysis unit 700 predicts the health of the corresponding user based on the retrieved similar cases and proposes guidelines for improving health at step S36. The predicted personal health information and the proposed guidelines may be delivered to the healthcare platform 300 via the health analysis result provision unit 600.

Accordingly, the health analysis result provision unit 600 of the analysis platform 400, connected to the healthcare platform 300, may provide the analysis result, which makes it possible to provide health service customized for the corresponding user, at step S38. For example, predicted health information, guidelines for improving health, and the like are provided to the corresponding user.

The participation of various health service providers through the Open API of the healthcare platform 300 may lead to various customized services based on the information in the health-related big data repository 50.

Figure 6:
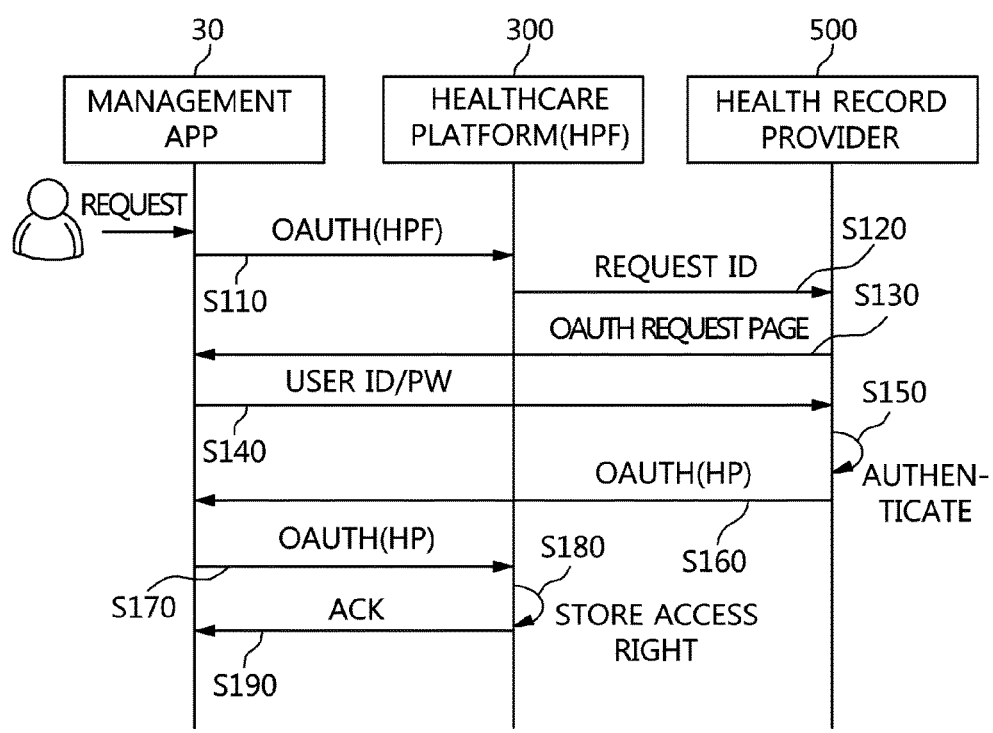
FIG. 6 is a flowchart illustrating the process of registering for the right to access a health record provider in a healthcare platform on a per-user basis in an open healthcare apparatus and method according to an embodiment of the present invention.

FIG. 6 is a flowchart illustrating the process of registering for the right to access a health record provider in a healthcare platform on a per-user basis in an open healthcare apparatus and method.

As described above, the healthcare platform 300 provides the Open API 34 for interconnecting a user terminal, a health record provider 500, a personal cloud repository 40, various health service institutes, and the like, and includes a health record adapter 32, which functions as a framework for relaying data transmitted during the interconnection process.

Meanwhile, the health record adapter 32 may be configured to include the personal health data processing unit 100 and the public health data processing unit 200, as described above.

Here, the healthcare platform 300 does not grant the right to access the connected user terminal, health record provider 500, personal cloud repository 40, or various service institutes, but sets and confirms the user's right to access the system connected to the healthcare platform 300 in order to secure integrity for preventing both unauthorized access to the electronic records and damage, falsification, and deletion of the electronic records.

Also, as described above, the user voluntarily opens his or her health data, and stores the personal health record in the personal cloud repository 40 to be managed.

In order to store the user's health record in the personal cloud repository 40, the user selects at least one health record provider 500 and stores the records in the personal cloud repository 40 through the healthcare platform 300.

Also, as described above, because existing health record data use independent formats for various respective health service institutes, the data are converted into health data that may be accommodated by all of the service institutes. Here, the conversion into the health data may be individually performed by the health service institutes, but it is desirable that the health record adapter 32 of the healthcare platform 300 perform the conversion.

As illustrated in FIG. 6, in order to receive user's health records from the health record provider 500, it is necessary to register for the right to access the health record provider 500 in the healthcare platform 300. Namely, in order to collect personal health records from the health record provider 500 through the healthcare platform 300, access privileges must be granted by the health record provider 500.

First, the user selects the at least one health record provider 500 and requests the registration through the management app 30, provided and authenticated by the healthcare platform 300, at step S110.

Next, the healthcare platform 300 provides the user's request to the health record provider 500 at step S120. The health record provider 500 that receives the request provides a login page for authentication in response to the request through the management app 30 installed in the user's terminal, rather than through the healthcare platform 300, at step S130.

The user inputs the user ID and password that were provided to the health record provider 500 when joining, in the login page displayed in the user terminal to authenticate the user at step S140.

Next, the health record provider 500 authenticates the user using the input user ID and password at step S150, and transmits information about the right to access the corresponding health record provider 500 to the management app 30 installed in the user terminal at step S160.

Next, the management app 30, which received the access right, transmits its access right to the healthcare platform 300 to enable the healthcare platform 300 to access the health record provider 500 at step S170.

Next, the healthcare platform 300 receives and stores the access right at step S180, and transmits an acknowledge signal to the user terminal through the management app 30 at step S190, whereby the user may receive the personal health record provided by the health record provider 500 through the healthcare platform 300.

Meanwhile, the access right may be stored in the form of an access token in the case of OAuth, which is an international standard for authorization, or may be a certificate in the case where the access right is set using a certificate of the type commonly used in the financial industry.

Consequently, storing the token of the health record provider 500 in the healthcare platform 300 through the management app 30 becomes a means for being immediately provided with the health record from the health record provider 500 through the healthcare platform 300.

Figure 7:
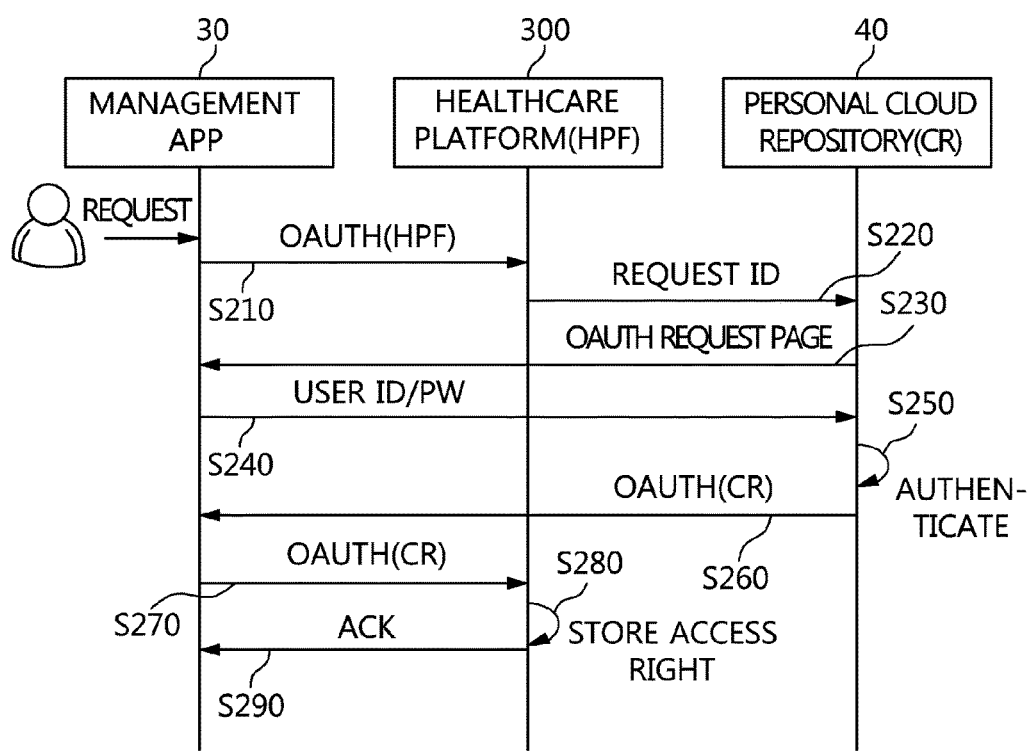
FIG. 7 is a flowchart illustrating the process of registering for the right to access a personal cloud repository in a healthcare platform on a per-user basis in an open healthcare apparatus and method according to an embodiment of the present invention.

FIG. 7 is a flowchart illustrating a process for registering for the right to access the personal cloud repository in the healthcare platform on a per-user basis in an open healthcare apparatus and method.

As illustrated in FIG. 7, at step S210, the user requests the connection to the personal cloud repository 40 from the healthcare platform 300 through the management app 30 provided by the healthcare platform 300.

Next, the healthcare platform 300 delivers the user's request to the personal cloud repository 40 at step S220, and the personal cloud repository 40 displays a page prompting for a user ID and password for user authentication through the management app 30 of the user terminal at step S230.

Next, when the user inputs the user ID and password at step S240, the personal cloud repository 40 authenticates the user using the user ID and password at step S250 and transmits the access right to the management app 30 of the user terminal at step S260.

Next, the user receiving the access right transmits information about the access right to the healthcare platform 300 to enable access to the personal cloud repository 40 at step S270.

Next, the healthcare platform 300 receives and stores the access right at step S280 and transmits an acknowledge signal at step S290, whereby the healthcare platform 300 may store the user's personal health records in the personal cloud repository 40 and manage and access the records stored in the personal cloud repository 40.

Figure 8:
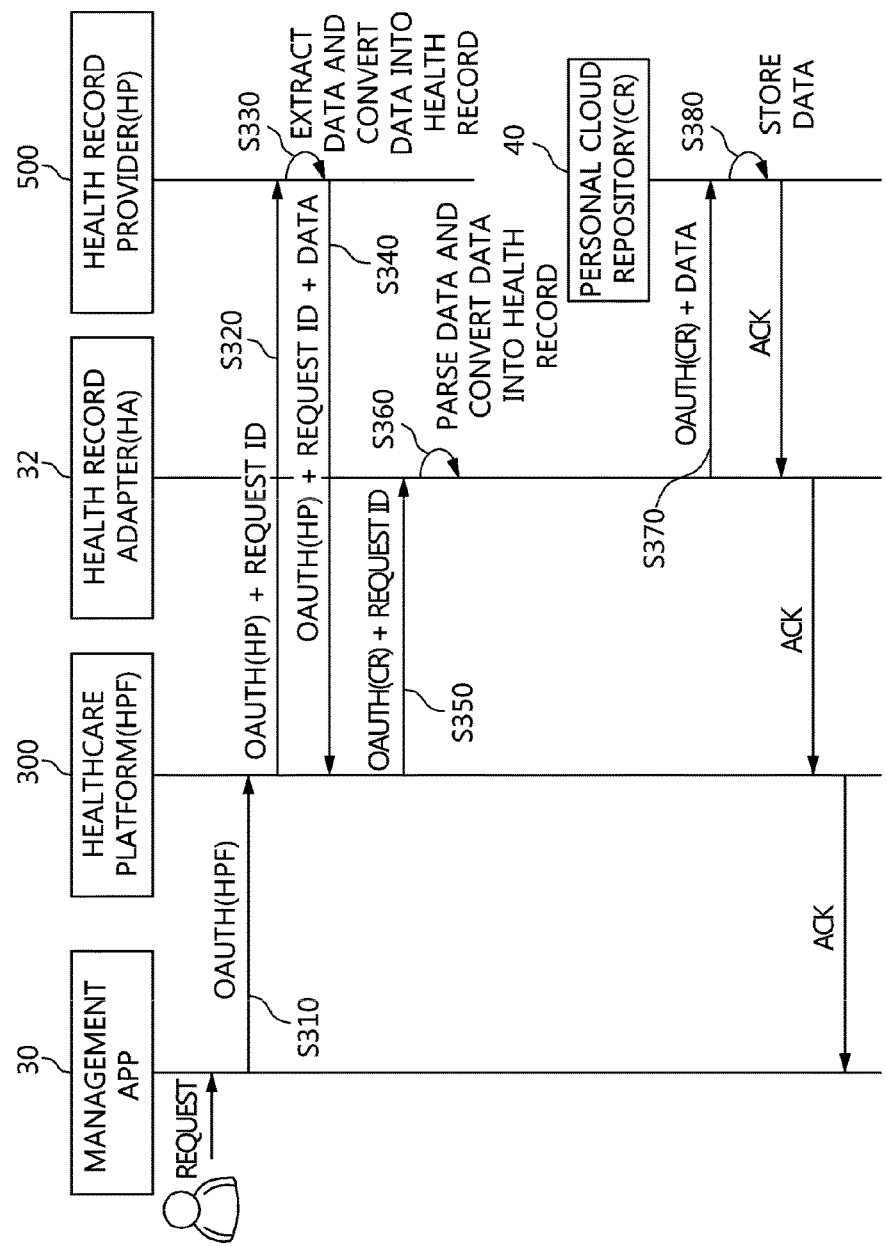
FIG. 8 is a flowchart illustrating the process in which a user retrieves a personal health record from a health record provider, converts the records in a healthcare platform, and stores them in a personal cloud repository, in an open healthcare apparatus and method according to an embodiment of the present invention.

FIG. 8 is a flowchart illustrating a process in which a user retrieves a personal health record from the health record provider, converts the record in the healthcare platform, and stores it in the personal cloud repository in an open healthcare apparatus and method.

Meanwhile, in order for a user to retrieve a personal health record from the health record provider 500 and store it in the personal cloud repository 40, the user must be registered in the health record provider 500 and the right to access the personal cloud repository 40 must be set in advance.

Because the process of registering for the right to access the health record provider 500 and the process for setting the right to access the personal cloud repository 40 have been described with reference to FIGS. 6 and 7, a detailed description thereof will be omitted.

As illustrated in FIG. 8, using the management app 30, a user retrieves a personal health record from the health record provider 500 via the healthcare platform 300 and stores the personal health record in the personal cloud repository 40 to manage and access it.

First, the user selects at least one from among multiple health record providers 500, registered in the healthcare platform 300 through the management app 30, and requests the healthcare platform 300 to store the user's personal health record in the personal cloud repository 40 at step S310.

Next, the healthcare platform 300 transmits information about the access right of the user and the service request of the user to the selected health record provider 500 at step S320.

Next, the health record provider 500 extracts the personal health record of the user from its database using the user's service request, converts the extracted personal health record into a health record at step S330, and transmits it along with the token of the health record provider 500 and an ID for the service request to the healthcare platform 300 at step S340.

Meanwhile, the health record is a personal health record converted into a data format that may be accommodated by the healthcare platform 300, and the conversion into the health record may be performed by the health record provider 500, but it is desirable for the conversion to be performed in the health record adapter 32 of the healthcare platform, as described above.

Next, the healthcare platform 300 receiving the health record transmits information about the right (i.e. the token) for accessing the personal cloud repository 40 and the health record to the health record adapter 32, which serves to relay data, at step S350.

Next, if the personal health record is transmitted without conversion into the health record according to the healthcare platform in the health record provider 500, the health record adapter 32 parses the personal health record, converts it into a format to be stored in the personal cloud repository 40 at step S360, and transmits it together with the token for the personal cloud repository 40 at step S370. Then, the personal cloud repository 40 stores the transmitted health record therein at step S380.

Figure 9:
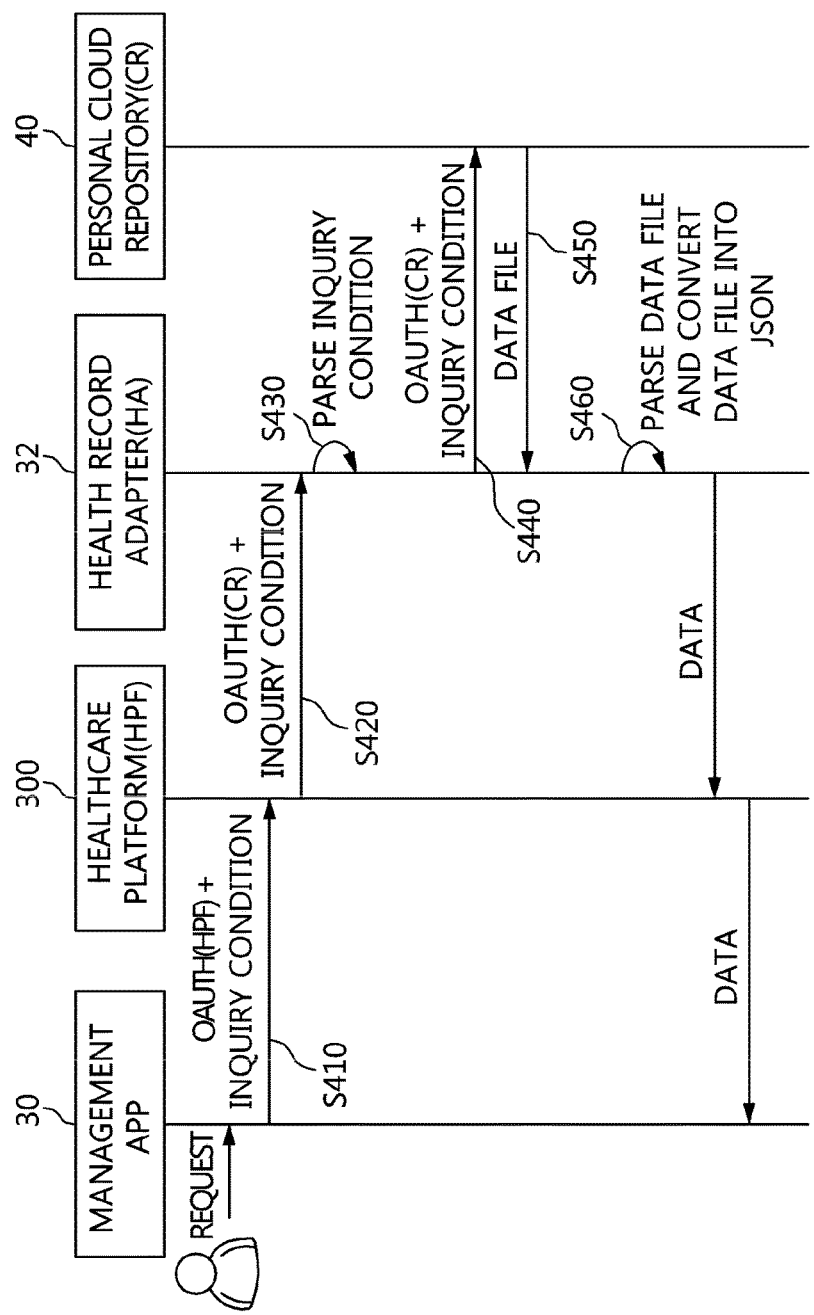
FIG. 9 is a flowchart illustrating the process in which a user retrieves a health record from a personal cloud repository in an open healthcare apparatus and method according to an embodiment of the present invention.

FIG. 9 is a flowchart illustrating a process in which a user retrieves a health record from the personal cloud repository in an open healthcare apparatus and method.

First, a user transmits an inquiry condition for retrieving his or her health record stored in the personal cloud repository 40 to the healthcare platform 300 through the management app 30 at step S410.

Next, the healthcare platform 300 transmits information about the right to access the personal cloud repository 40 and the inquiry condition to the health record adapter 32 at step S420.

Next, the health record adapter 32 parses the inquiry condition at step S430, and transmits the received access right and the inquiry condition to the personal cloud repository 40 at step S440. The personal cloud repository 40 retrieves the health record using the inquiry condition, and transmits the retrieved data file to the health record adapter 32 at step S450.

Next, the health record adapter 32 parses the received data file and converts the data into a JavaScript Object Notation (JSON) format at step S460, to enable the user to easily read the retrieved record, and transmits it.

Here, JSON is a lightweight data exchange format, easily analyzed and generated by a machine, and is configured as a human-readable/writable text format. The converted data is transmitted to the management app 30 through the healthcare platform 300, whereby the user may check the data.

Figure 10:
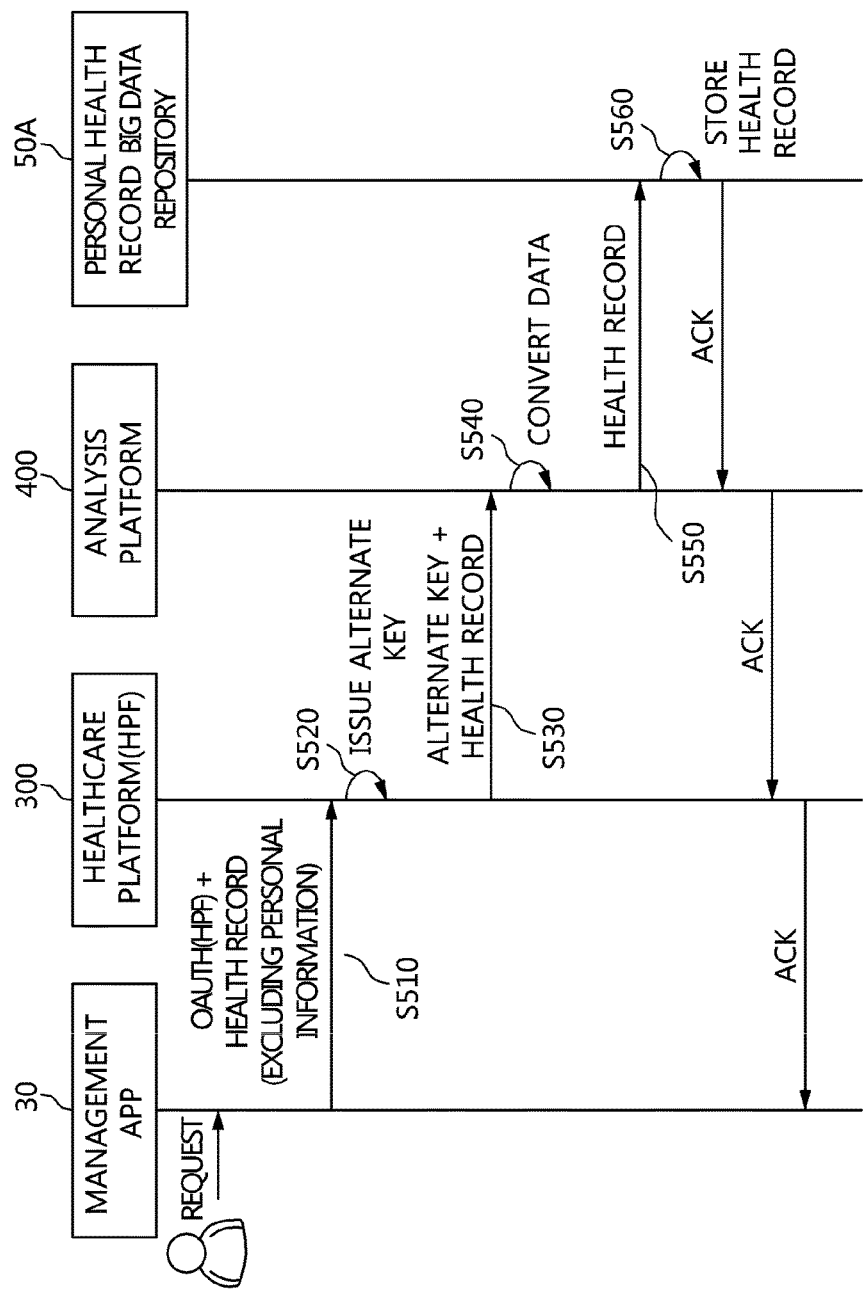
FIG. 10 is a flowchart illustrating the process in which a user provides a personal health record to a personal health record big data repository 50A to be stored through a healthcare platform 300 in an open healthcare apparatus and method according to an embodiment of the present invention.

FIG. 10 is a flowchart illustrating the process in which a user provides a personal health record to the personal health record big data repository 50A to be stored through the healthcare platform 300 in an open healthcare apparatus and method.

As illustrated in FIG. 10, a user transmits his or her health record, from which personal information has been deleted, to the healthcare platform 300 through the management app 30 at step S510. Meanwhile, it is assumed that the health record has been stored in the personal terminal by retrieving some or all of the health records of the user from the personal cloud repository 40 through the retrieval process described in FIG. 9.

Also, the provision of the personal health record to the healthcare platform 300 is performed by the management app 300, but may alternatively be performed by a service app provided by various healthcare service institutes.

Next, the healthcare platform 300 issues an alternate key to the personal health record at step S520 and transmits it to the analysis platform 400 at step S530. Here, the reason why the alternate key is issued is to enable the big data repository to consistently store health records by confirming whether a newly provided health record is consistent with existing health records when the user additionally provides the newly generated health record under the condition that his or her health record has been provided to the big data repository. Also, because information about the user's future health, analyzed and provided by the analysis platform 400, is predicted based on similar cases, the alternate key may be used to prevent the user's own data from being included in the resultant retrieved similar cases.

Next, the analysis platform 400 transmits the received personal health record to the personal health record big data repository at step S550 and stores it at step S560. Meanwhile, when the personal health record is transmitted to the analysis platform 400 without conversion into a format to be stored in the personal health record big data repository, the analysis platform 400 converts the personal health record into a format to be stored in the personal health record big data repository at step S540.

Figure 11:
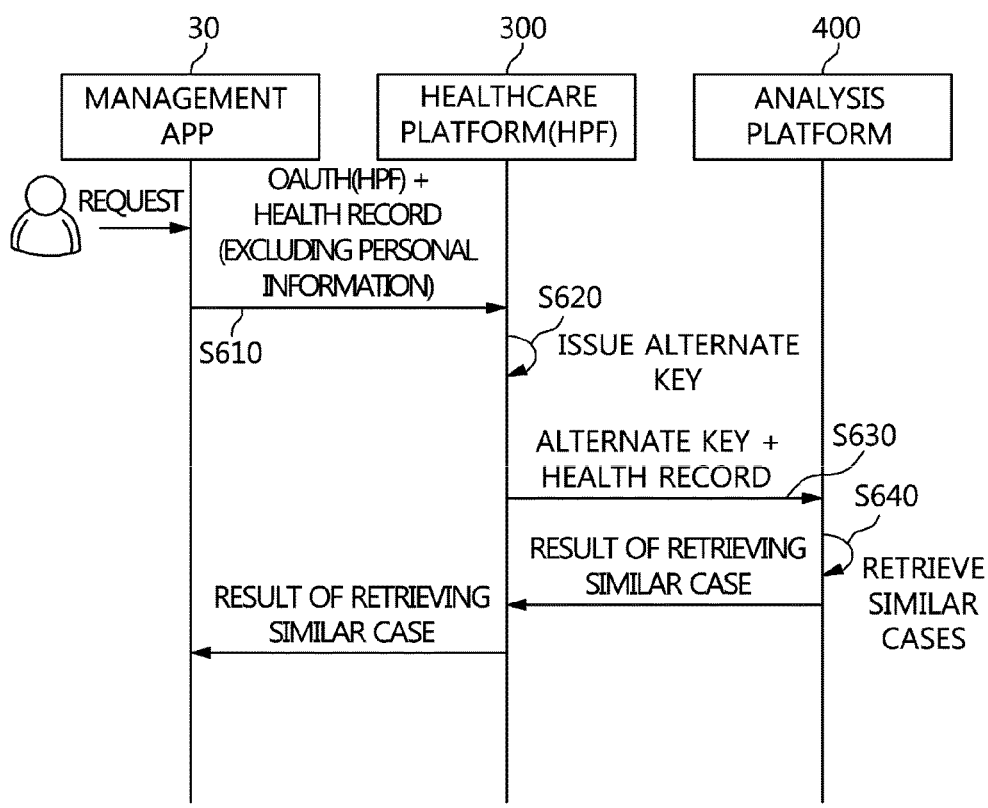
FIG. 11 is a flowchart illustrating a process for retrieving similar cases in an analysis platform in an open healthcare apparatus and method according to an embodiment of the present invention.

FIG. 11 is a flowchart illustrating a process for retrieving a similar case in the analysis platform 400 in an open healthcare apparatus and method.

First, a user requests the healthcare platform 300 to retrieve similar cases while transmitting a health record, from which the user's personal information has been deleted, through the management app 30 at step S610. Also, it is assumed that the health record has been stored in the personal terminal by retrieving some or all of the health records of the user from the personal cloud repository 40 through the retrieval process described in FIG. 9.

The provision of the personal health record to the healthcare platform 300 is performed by the management app 30, but may be performed by a service app provided by various healthcare service institutes.

Next, the healthcare platform 300 issues an alternate key to the health record of the corresponding user at step S620, and transmits the health record with the alternate key to the analysis platform 400 at step S630. The analysis platform 400 retrieves similar cases based on the received health record at step S640, and transmits the result of retrieval of similar cases to the healthcare platform 300. Then, the healthcare platform 300 provides the result of retrieval the similar cases to the user through the management app 30, whereby the retrieval of similar cases may be accomplished.

Figure 12:
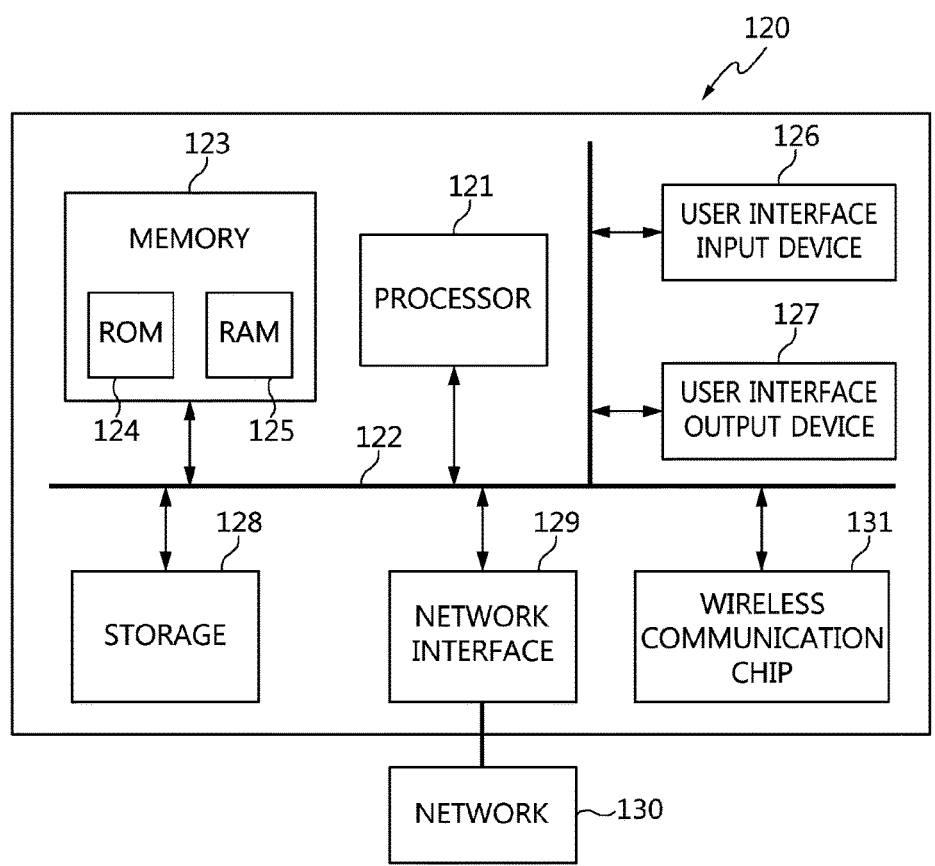
FIG. 12 is a view illustrating a computer system in which an embodiment of the present invention is implemented.

Meanwhile, the above-mentioned embodiment of the present invention may be implemented in a computer system such as a computer-readable storage medium. As illustrated in FIG. 12, a computer system 120 may include one or more processors 121, memory 123, a user interface input device 126, a user interface output device 127, and storage 128, which communicate with each other through a bus 122. Also, the computer system 120 may further include one or more network interfaces 129 that are connected to a network 130. The processors 121 may be a semiconductor device for executing processing instructions stored in a central processing unit, the memory 123, or the storage 128. The memory 123 and the storage 128 may be various types of volatile or non-volatile storage media. For example, the memory 123 may include ROM 124 or RAM 125.

Also, if the computer system 120 is implemented as a small size of computing device to prepare for IoT, when an Ethernet cable is connected to the computing device, the computing device may be operated as a wireless router. In this case, because a mobile device may wirelessly connect to the gateway and perform encryption and decryption functions, the computer system 120 may further include a wireless communication chip (a Wi-Fi chip) 131.

Therefore, the embodiment of the present invention may be implemented as a method implemented by a computer or a non-volatile computer-readable medium in which instructions executable by a computer are recorded. When computer-readable instructions are executed by a processor, the computer-readable instructions may perform the method according to at least one aspect of the present invention.

According to the present invention as configured above, because the rights to personal health records (information, data) are granted to individuals, problems concerning personal information protection and medical law may be avoided.

Also, because the present invention defines an integrated health record (in an XML format) capable of accommodating EMR from medical clinics and hospitals, health records about oriental medicine, fitness data, and the like, integrated management of health records such as bio-signals, life habits, etc. is feasible. Accordingly, user convenience may be improved. Also, because various types of data may be used, the accuracy and diversity of analysis and services may be realized.

In healthcare, changes in the health of people similar to a user is very important data to be examined by the user and medical teams. The present invention constructs a health-related big data repository by continuously updating public health data and health data provided by individuals, whereby various customized health services are available and the reliability of the services may be improved.

Interconnection with various health record providers, improvement in the reliability of service through the construction of a health-related big data repository, and the construction of an open platform in which users and service providers may voluntarily participate may contribute to a healthcare ecosystem.

As described above, optimal embodiments of the present invention have been disclosed in the drawings and the specification. Although specific terms have been used in the present specification, these are merely intended to describe the present invention, and are not intended to limit the meanings thereof or the scope of the present invention described in the accompanying claims. Therefore, those skilled in the art will appreciate that various modifications and other equivalent embodiments are possible from the embodiments. Therefore, the technical scope of the present invention should be defined by the technical spirit of the claims.

What is claimed is:

1. An open healthcare apparatus, comprising:
   a healthcare platform providing an Open API enabling provision of a customized service; and
   an analysis platform,
   wherein the healthcare platform comprises:
   a personal health data processing unit receiving personal health data of a user from a plurality of health record providers, converting the personal health data into an identical format, and storing the converted personal health data in a personal cloud repository, the identical format being an XML format; and
   a public health data processing unit receiving public health data from a public health data server, converting the public health data into the XML format, and storing the converted public health data in a health-related big data repository on a health case basis, wherein the analysis platform comprises:

a health data analysis unit generating an analysis result by analyzing the converted personal health data based on the public health data stored in the health-related big data repository; and a health analysis result provision unit providing the user with a customized service by providing the analysis result to the healthcare platform, and wherein the personal health data processing unit performs:

receiving, from a user terminal, a first access right issuing request for a health record provider selected from among the plurality of health record providers, wherein the selected health record provider is selected by the user and accessible by the user through a first personal authentication;

transferring the first access right issuing request to the selected health record provider, and acquiring a first access right from the selected health record provider when the first personal authentication is performed by the user on the selected health record provider;

receiving, from the user terminal, a second access right issuing request for the personal cloud repository, wherein the personal cloud repository is selected from among a plurality of personal cloud repositories and accessible by the user through a second personal authentication;

transferring the second access right issuing request to the selected personal cloud repository, and acquiring a second access right from the selected personal cloud repository when the second personal authentication is performed by the user on the selected personal cloud repository;

receiving, from the user terminal, a request for storing personal health data provided by the selected health record provider; and receiving the personal health data from the selected health record provider using the first access right and storing the personal health data in the selected personal cloud repository using the second access right.

2. The open healthcare apparatus of claim 1, wherein the personal health data processing unit converts the personal health data by performing communication, authentication, and data transmission with the plurality of health record providers through the healthcare platform.

3. The open healthcare apparatus of claim 1, wherein the health-related big data repository stores health data provided by the personal cloud repository under agreement of the user, the public health data provided by the public health data server, or a combination thereof.

4. The open healthcare apparatus of claim 1, wherein the health data analysis unit generates the analysis result by:
retrieving a case similar to the personal health data of the user by mining the public health data stored in the health-related big data repository;
predicting the future health of the user based on the retrieved similar case; and
proposing a guideline for improving the future health of the user.

5. The open healthcare apparatus of claim 1, wherein the plurality of health record providers include a server of at least one western medicine hospital, a server of at least one oriental medicine hospital, a life log server, or a combination thereof.

6. An open healthcare method performed by an open healthcare apparatus, the method comprising:

receiving, from a user terminal, a first access right issuing request for a health record provider selected from among a plurality of health record providers, wherein the selected health record provider is selected by a user and accessible by the user through a first personal authentication;

transferring the first access right issuing request to the selected health record provider, and acquiring a first access right from the selected health record provider when the first personal authentication is performed by the user on the selected health record provider;

receiving, from the user terminal, a second access right issuing request for a personal cloud repository, wherein the personal cloud repository is selected from a plurality of personal cloud repositories and accessible by the user through a second personal authentication;

transferring the second access right issuing request to the selected personal cloud repository, and acquiring a second access right from the selected personal cloud repository when the second personal authentication is performed by the user on the selected personal cloud repository;

receiving, from the user terminal, a request for storing personal health data provided by the selected health record provider;

receiving the personal health data from the selected health record provider using the first access request;

converting the personal health data into an identical format, the identical format being an XML, format;

storing the converted personal health data in the selected personal cloud repository using the second access right, and performing integrated management on the personal health data;

analyzing health-related big data that includes public health data and the personal health data in the selected personal cloud repository, the public health data being in the XML format; and providing a customized health service to the user based on the analyzed health-related big data.

7. The open healthcare method of claim 6, wherein converting the personal health data into the identical format includes performing communication, authentication, and data transmission with a plurality of personal health data servers through a healthcare platform, the plurality of personal health data servers respectively corresponding to the plurality of health record providers.

8. The open healthcare method of claim 6, further comprising:
receiving the public health data from a public health data server,
converting the received public health data into the XML format using a public health data processing unit; and
storing the converted public health data in a health-related big data repository.

9. The open healthcare method of claim 6, wherein storing the converted personal health data in the selected personal cloud repository includes transmitting the converted personal health data to the selected personal cloud repository through health data relay by a healthcare platform without storing the converted personal health data in the user terminal of the user.

10. The open healthcare method of claim 6, wherein the health-related big data is health data being provided by the selected personal cloud repository under agreement of the user, the public health data being provided by a public health data server, or a combination thereof.

11. The open healthcare method of claim 6, wherein providing the customized health service comprises:
   retrieving a case similar to the personal health data of the user by performing data mining on the health-related big data; and
   predicting the future health of the user based on the retrieved similar case; and proposing a guideline for improving the future health of the user.

* * * * *